United States Patent

Van Egeraat

[11] Patent Number: 5,914,997
[45] Date of Patent: Jun. 22, 1999

[54] X-RAY SPECTROMETER WITH AN ANALYZER CRYSTAL HAVING A PARTLY VARIABLE AND A PARTLY CONSTANT RADIUS OF CURVATURE

[75] Inventor: Walterus A. L. A. Van Egeraat, Almelo, Netherlands

[73] Assignee: U.S. Philips Corporation, New York, N.Y.

[21] Appl. No.: 08/990,215

[22] Filed: Dec. 12, 1997

[30] Foreign Application Priority Data

Dec. 20, 1996 [EP] European Pat. Off. ............ 96203653

[51] Int. Cl.⁶ .................................................. G01N 23/00
[52] U.S. Cl. ................................................ 378/45; 378/84
[58] Field of Search ............................ 378/45, 49, 81, 378/82, 84, 85

[56] References Cited

U.S. PATENT DOCUMENTS

| | | | |
|---|---|---|---|
| 3,439,163 | 4/1969 | De Jongh | 378/84 |
| 4,351,063 | 9/1982 | Dineen et al. | 378/79 |
| 4,562,585 | 12/1985 | Gobel et al. | 378/83 |
| 4,949,367 | 8/1990 | Huizing et al. | 378/84 |
| 5,406,609 | 4/1995 | Arai et al. | 378/73 |
| 5,757,883 | 5/1998 | Haisma et al. | 378/84 |

OTHER PUBLICATIONS

"Principles and Practice of X–Ray Spectrometric Analysis" 2nd ed. by Eugene P. Bertin, Plenum Press, New York–London (ISBN 0–306–30809–6), chapter 5.5, notably chapter 5.5.3.1–5.5.3.3.

*Primary Examiner*—David P. Porta
*Attorney, Agent, or Firm*—Anne E. Barschall

[57] ABSTRACT

An imaging optical system having a Rowland geometry can be used in a spectrometer for X-ray fluorescence. For the focusing of the X-ray beam emanating from the specimen to be analyzed use is made of a curved analyzer crystal 28 whose radius of curvature may be variable, as in the case of a crystal surface 29 in the form of a logarithmic spiral 40. If such an analyzer crystal is to be made sufficiently large so as to achieve adequate intensity in the X-ray detector, a part of the crystal would have to be given a radius of curvature which is smaller than permissible so as to avoid fracturing of the crystal. In accordance with the invention, a first part 40 of the reflective surface 29 has a radius of curvature which is dependent on the location on the crystal whereas another part 42 of the reflective surface has a constant radius of curvature 44. A crystal part having a constant radius of curvature exhibits angular deviations, but for as long as these angular deviations are smaller than a given (not very low) limit value, they can be ignored in relation to other, larger deviations of the log spiral part. Such larger deviations occur notably when a multilayer mirror is chosen for the analyzer crystal 28.

6 Claims, 2 Drawing Sheets

X-RAY SPECTROMETER WITH AN ANALYZER CRYSTAL HAVING A PARTLY VARIABLE AND A PARTLY CONSTANT RADIUS OF CURVATURE

The invention relates to an apparatus for the analysis of materials by means of X-ray fluorescence, including:
a specimen location for receiving a specimen of the material to be analyzed,
an X-ray source for irradiating the specimen location by means of X-rays,
an analyzer crystal which has a curved reflective surface for wavelength analysis of fluorescent radiation produced by the specimen,
a detector for detecting the radiation emanating from the analyzer crystal.

The invention also relates to an analyzer crystal for use in such an X-ray spectrometer.

An apparatus of this kind is known from "Principles and Practice of X-Ray Spectrometric Analysis" $2^{nd}$ ed. by Eugene P. Bertin, Plenum Press, New York-London, (ISBN 0-306-30809-6), chapter 5.5, notably chapter 5.5.3.1.–5.5.3.3.

Generally speaking, X-rays (fluorescent radiation) are generated in a specimen to be analyzed in an X-ray spectrometer; this radiation is characteristic of the elements and chemical combinations present in the specimen. The fluorescent radiation can be excited in the specimen by X-rays from an X-ray source which is usually an X-ray tube. The fluorescent radiation excited in the specimen has a more or less broad spectrum of wavelengths which are present in the spectrum with a given intensity distribution which is characteristic of the composition of the specimen.

It may occur that the user of an X-ray spectrometer is interested only in the intensity of one wavelength, i.e. one "spectral line", or in a number of wavelengths which are situated near one another. This situation occurs when the content of a given chemical element is to be determined in the specimen to be analyzed.

Thus, because the intensity of the fluorescent radiation is to be found for one wavelength or for a few wavelengths which are situated near one another, the fluorescent radiation must be analyzed according to wavelength, i.e. the intensity analysis. This can be performed by conducting the fluorescent radiation to an analyzer crystal. This analysis is based on the well-known Bragg relation: $2d \cdot \sin\nu = n\lambda$, where d is the distance between the X-ray reflective crystal faces in the analyzer crystal, $\nu$ is the angle of incidence of the radiation to be analyzed on the analyzer crystal, $\lambda$ is the wavelength of the reflected radiation, and n is an integer. Measurement of the intensity of the radiation which is incident at a given angle $\nu$ relative to the lattice planes of the analyzing crystal and is reflected at the same angle again thus reveals the wavelength having this intensity. The intensity of the relevant wavelength can then be measured by means of a customary detector.

It is to be noted that in this context the term "analyzer crystal" is to be understood to mean not only real crystals, but also multilayer mirrors for X-rays which are known per se. Such a mirror consists of a stack of different, layers of comparatively small thickness, for example 2 nm. Such a mirror also enables measurement of long-wave X-rays as opposed to natural crystals which practically always have a lattice constant, and hence an associated distance of the reflective crystal faces, which is too small for reflection of such long-wave X-rays. This limitation of the wavelength to be reflected is also revealed by the above-mentioned Bragg relation.

In order to achieve a suitable resolution and sensitivity, and hence a suitable measuring accuracy, X-ray spectrometers are provided with a so-called focusing optical system which means in this context that the source of the radiation to be analyzed (i.e. the specimen to be examined or an entrance slit situated in the beam path preceding it) is imaged on the X-ray detector (or an exit slit situated in the beam path preceding it) by the analyzer crystal. This imaging effect is obtained by constructing the analyzer crystal so as to have a curved surface, so that the analyzer crystal has not only an analyzing function but also an imaging function. In order to ensure that the focusing condition is still satisfied, the specimen (or the entrance slit) as well as the analyzer crystal and the detector (or the exit slit) should remain situated on a given circle, the so-called Rowland circle, while successively passing through all values of $\nu$, the diameter of said Rowland circle being determined by the radius of curvature of the analyzer crystal. The curvature of the analyzer crystal is then defined by the rule that the radius of curvature at the area of the point of tangency of the crystal to the Rowland circle must be equal to the diameter of this circle.

The cited book by Bertin describes analyzer crystals of various shapes and various curvatures, including a customary analyzer crystal in the form of a log spiral. Such log spiral analyzer crystals have a number of advantages and a number of drawbacks. It is an advantage of log spiral analyzer crystals that in this type of analyzer crystal said Bragg relation is satisfied across the entire surface of the analyzer crystal if it is exposed to a non-parallel beam, i.e. to a beam which originates or seems to originate from one point, as is the case in the above Rowland configuration. This means that the entire crystal surface contributes to the intensity of the X-rays to be analyzed, so that a high signal-to-noise ratio is obtained for the measurement. Moreover, because each surface element is in principle irradiated at the same, correct Bragg angle, this type of analyzer crystal has a suitable wavelength selectivity.

Drawbacks of log spiral analyzer crystals are:
1) Because the radius of curvature of this type of analyzer crystal is not constant across the crystal surface, there are locations with a radius of curvature which is substantially smaller than the radius of curvature prescribed by the Rowland geometry. Therefore, it will often be difficult to manufacture a crystal of adequate dimensions, because the radius of curvature then becomes so small that the crystal (having the shape of a rectangular, thin plate in the non-distorted state) breaks during bending so as to obtain the desired log spiral shape.
2) Log spiral crystals image a point of the source of the radiation to be analyzed (i.e. the specimen to be examined or an entrance slit situated in the beam path preceding it) on the X-ray detector (or an exit slit situated in the beam path preceding it) with an imaging error which is larger than that of analyzer crystals having the same dimensions and a constant radius of curvature. Consequently, the entrance slit is imaged with a width which is (significantly) larger than its actual width. Therefore, the exit slit must be wider than the value corresponding to the width of the entrance slit, so that (significantly) more background radiation is intercepted by the detector, thus degrading the signal-to-noise ratio of the measurement.

An X-ray spectrometer aims to achieve a high wavelength resolution as well as a high intensity of the radiation in the detector. A high resolution yields a high degree of reliability concerning the composition of the specimen to be examined. A high intensity of the radiation in the detector ensures that the measuring times required to determine the composition of the specimens are short. This is very important in practice, because for some specimens the measuring time may be of the order of magnitude of one half hour. The number of specimens that can be examined per unit of time is an important aspect, notably in an industrial environment. The two above requirements are contradictory in a given sense, because in the case of suitable resolution only a small part of the radiation is detected, so that only a low intensity remains. Therefore, it is very important to ensure that the loss of radiation from the specimen is minimized on its way from the entrance slit to the detector. This is achieved by ensuring that as much radiation as possible is incident on the analyzer crystal and hence contributes to the desired high intensity.

It is an object of the present invention to provide an apparatus of the kind set forth for the examination of materials by means of X-ray fluorescence in which the amount of radiation reflected by the analyzer crystal is optimum.

To achieve this, the X-ray fluorescence apparatus according to the invention is characterized in that the analyzer crystal comprises two parts, being a first part which has a reflective surface which is curved in one direction with a radius of curvature which is dependent of the location on the crystal, the other part having a reflective surface which is curved with a constant radius of curvature in said direction.

For the first part of the analyzer crystal use can be made of an elongate thin plate of a crystal material which is bent in one plane, i.e. a plane is imagined perpendicularly to the surface of the crystal plane, the line of intersection of this imaginary plane and the crystal surface being situated in the longitudinal direction of the elongate crystal plate. The crystal plate is then bent in such a manner that the (initially straight) line of intersection becomes a curved line. Straight lines in the crystal surface which extend perpendicularly to the line of intersection then remain straight lines. Thus, a reflective surface is obtained which is curved in one plane with a radius of curvature which, if the line of intersection has not been bent so as to form a circle, is not constant and hence is dependent on the location on the crystal. If for some reason a decision is made in favor of a crystal surface having a non-constant radius of curvature, the situation occurs in which parts of said surface necessarily have a radius of curvature which is smaller than that of other parts, notably smaller than the radius of curvature prescribed by the Rowland geometry.

Because the aim is for a high intensity of the radiation in the detector, it is attempted to arrange the analyzer crystal as near to the entrance slit as possible, which means that preference is given to a geometry with an as small as possible Rowland circle. Consequently, the analyzer crystal must also have a small radius of curvature, which could result in fracturing of the crystal plate during its deformation aiming to achieve the desired radius of curvature. The first part of the analyzer crystal can now be chosen to be so long that the radius of curvature for which fracturing of the crystal plate would occur is just not reached. In order to obtain an as large as possible crystal surface nevertheless, the analyzer crystal can be continued with a part having a constant radius of curvature.

For this other part of the analyzer crystal use can be made of the same elongate thin crystal material which is also bent in said plane. If the line of intersection for said part is bent so as to form a circle, the radius of curvature thereof will be constant in said plane.

A crystal part having a constant radius of curvature exhibits angular deviations (i.e. deviations of the angle of incidence which occur because the rays which are incident near the edges of the crystal are incident at an angle which is larger than that of the rays incident at the center), but these angular deviations can be ignored, provided that they are smaller than a predetermined (not very low) limit value, in comparison with other, larger deviations. Such larger deviations occur notably when a multilayer mirror as mentioned above is chosen for the analyzer crystal. It is a known property of such multilayer mirrors that the wavelength reflected according to the Bragg relation is not one well-defined wavelength and that a comparatively wide (in comparison with natural crystals) range around said wavelength (having a width which corresponds to an angular range of the order of magnitude of 2°) is also reflected. This range is known as the "rocking width" of the crystal. Therefore, if a multilayer mirror is chosen for the part having a non-constant radius of curvature, this part already exhibits a given spread in the wavelength to be reflected, which phenomenon has the same effect as the previously mentioned angular deviation. Therefore, if it is ensured that the angular deviation caused by the part of constant radius of curvature is negligibly small in comparison with the rocking width of the entire crystal, a gain can be made as regards the dimensions of the crystal without giving rise to an increased angular deviation. The present invention is based on the recognition of this fact.

The first part in an embodiment of the invention has a reflective surface which is curved in the form of a logarithmic spiral.

As a result of this step, optimum use is made of the property of crystals in the form of a logarithmic spiral that the angular deviation can be equated to zero for all practical purposes, so that the contribution to the angular deviation by this part of the crystal is as small as possible and is determined exclusively by the rocking width of the crystal material in practical circumstances.

In a further embodiment of the invention, at both ends of the first part there is provided a part which has a reflective surface which is curved with a constant radius of curvature.

Even though the risk of fracturing due to a small radius of curvature is practically absent at the least-curved side of the part having the non-constant radius of curvature, a cylindrical part can also be provided at that side. The manufacture is thus simplified in some cases.

The invention will be described in detail hereinafter with reference to the Figures in which corresponding reference numerals denote corresponding elements; therein:

Figure 1:
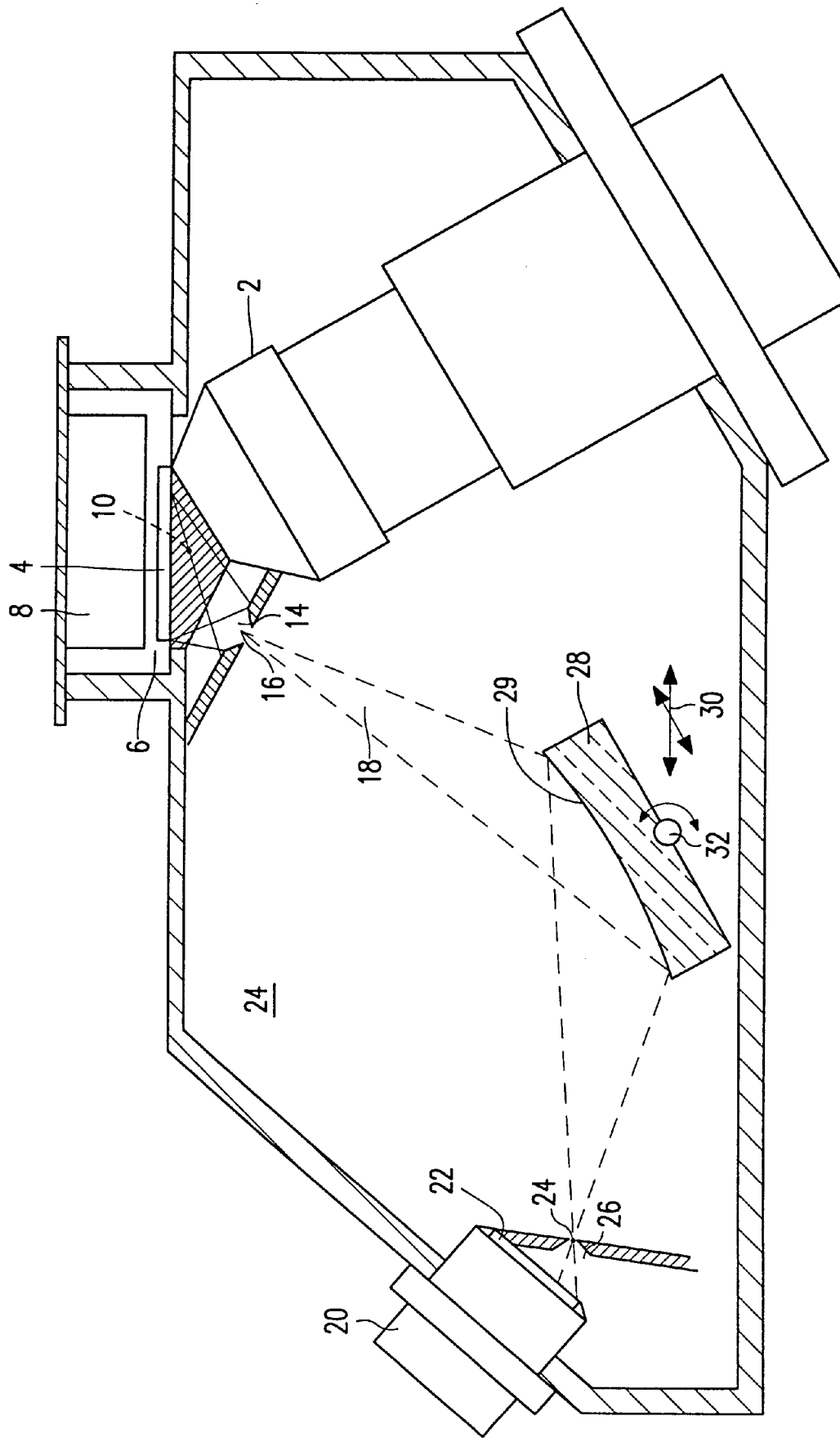
FIG. 1 is a partly sectional view of a part of the X-ray spectrometer which is of relevance to the invention.

FIG. 1 shows a part of an X-ray spectrometer which is of relevance to the invention. The X-ray spectrometer includes an X-ray tube 2 for generating an X-ray beam 10. The beam 10 irradiates a specimen 4 of a material to be analyzed by means of the X-ray spectrometer; the specimen is arranged in a specimen location for accommodating the specimen. To the present invention it is not of relevance that the X-ray fluorescent radiation is generated in the specimen by means of X-rays emanating from an X-ray tube; it is also feasible to irradiate the specimen by means of, for example electrons whereby X-rays are generated in the specimen.

The specimen 4 is arranged in a specimen holder 6 in a separate specimen chamber 8. In the specimen X-ray fluorescent radiation is generated which propagates in all directions as denoted by solid lines in the Figure. The fluorescent radiation reaches an entrance slit 14, so that this entrance slit performs the function of object 16 to be imaged in the Rowland geometry to be described with reference to FIG. 2. For the sake of clarity, the width of the slit 14 is not shown to scale in the Figure; in practical circumstances the width of the slit is of the order of magnitude of from some tens of microns to some millimeters, depending on the application. After having left the entrance slit 14, the beam of fluorescent radiation 18 is incident on an analyzer crystal 28 having a curved reflective surface 29. The shape of the surface will be described in detail with reference to FIG. 3. At this point it is to be noted merely that the surface 29 of the analyzer crystal 28 has a cylindrical shape, i.e. the line of intersection of the crystal surface with the plane of drawing is a curved line (i.e. the line 29 in the Figure), but the line of intersection of the crystal surface with a plane perpendicular to the plane of drawing (for example, the plane perpendicular to the plane of drawing and also perpendicular to the line 29) is a straight line. In this arrangement the analyzer crystal has a dual function: it selects the desired wavelength, determined by the angle of incidence v, from the beam of fluorescent radiation on the basis of said Bragg relation ($2d \cdot \sin v = n\lambda$), and it focuses the beam originating from the apparent object point 16 in the image point 24. This image point is imaged on an exit slit 26 which constitutes the entrance collimator for an X-ray detector 20. The X-rays thus reflected are incident, via an entrance window 22, in the detector 20 in which they are detected, after which further signal processing by means of electronic means (not shown) takes place.

The analyzer crystal 28 is mounted on a holder which is not shown in the Figure and is displaceable in two directions in the plane of drawing (as denoted by the arrows 30) and is also rotatable about an axis 32 which extends perpendicularly to the plane of drawing. As a result of these possibilities for displacement, the analyzer crystal can be adjusted so as to have an accurately defined orientation and position.

The beam path from the X-ray tube 2 to the detector 20 extends in a measuring space which can be hermetically sealed and, if desired, evacuated or filled with a gas suitable for the measurements.

Figure 2:
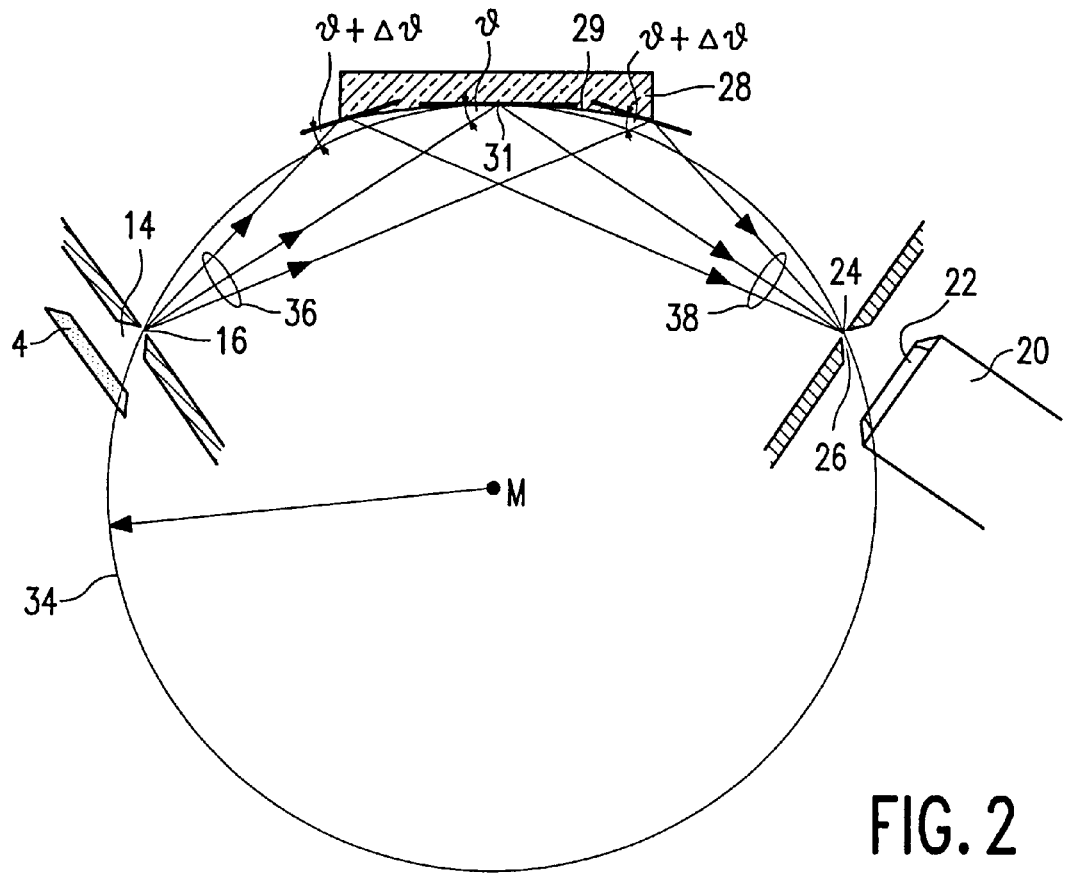
FIG. 2 shows a diagram illustrating the beam path in a Rowland geometry.

FIG. 2 shows a diagram illustrating the beam path in a Rowland geometry. The entrance slit 14 performs the function of object 16 to be imaged for the imaging Rowland geometry. Therein, the object 16 is situated on the Rowland circle 34 having a center M. The analyzer crystal 28 is arranged so that its surface 29 is tangent to the circle 24 in a point of tangency 31. The exit slit 24 is also arranged on the circle 34. The entrance slit 14 and the exit slit 24 are symmetrically situated relative to the point of tangency 31. The rays emanating from the object point 16 are incident on the analyzer crystal 28. A central ray of the beam 36 is incident at an angle v. When a circular shape is chosen for the crystal surface 29, the X-rays of the beam 36 enclose an angle $v + \Delta v$ relative to the crystal surface, where $\Delta v$ is the angular deviation. The radius of the circle constituting the crystal surface then equals, in conformity with the Rowland geometry, the diameter of the Rowland circle 34. The point A opposite the point of tangency 31 on the circle 34 thus constitutes the center of the crystal surface 29. Said angular deviation, however, equals zero if the shape of a logarithmic spiral is chosen for the crystal surface 29. After reflection on the crystal surface 29, the reflected beam 38 is focused in the image point 24, also being situated on the circle 34, and is then incident on the exit slit 24.

Figure 3:
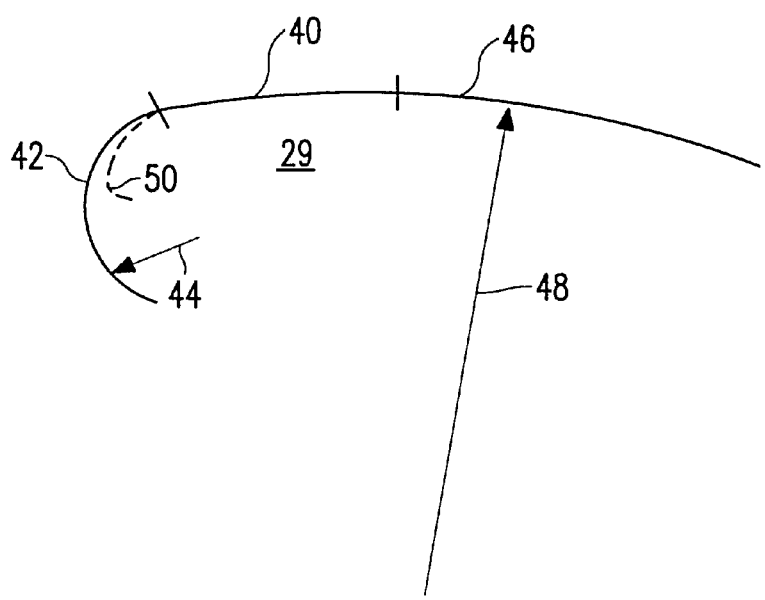
FIG. 3 shows diagrammatically a curved analyzer crystal according to the invention.

FIG. 3 shows diagrammatically the curved surface 29 of the analyzer crystal 28 according to the invention. Such a crystal can be produced by forming a plate from the desired crystal material (in the case of natural crystals) or from a manufactured multilayer mirror. A mould is made which has an inner surface which has the desired curved shape to be adopted by the crystal surface. The shape of said inner surface can be realized by means of any known manufacturing technique, for example milling by means of a numerically controlled milling machine. Any desired shape can thus be suitably approximated. Subsequently, the plate of the crystal material is pressed against the curved inner surface in the mould, so that the plate is elastically deformed and adopts the shape of the inner surface. The crystal is secured in position in this condition, for example by gluing.

The surface 29 can be subdivided into three parts: a first part 40 which is curved with a radius of curvature which is dependent on the location on the crystal, that is to say in the form of a logarithmic spiral; a second part 40 which is curved with a constant radius of curvature 44, so a circular shape; and a third part 46 which is curved with a constant radius of curvature 48, so again a circular shape. A dashed line 50 denotes the continuation of the logarithmic spiral, it clearly being shown that the radius of curvature of this part 50 continuously decreases along this line, i.e. that it has an increasingly larger curvature. This increasingly larger curvature is avoided by providing the circular part 42. It is to be noted that for the sake of clarity FIG. 3 is merely a diagrammatic representation of reality; in practical circumstances the curvatures of the surfaces 40, 42 and 46 will be substantially less.

I claim:

1. An apparatus for the analysis of materials by means of X-ray fluorescence, including:

a specimen location (6) for receiving a specimen (4) of the material to be analyzed, an X-ray source (2) for irradiating the specimen location by means of X-rays, an analyzer crystal (28) which has a curved reflective surface (29) for wavelength analysis of fluorescent radiation produced by the specimen (4), a detector (20) for detecting the radiation emanating from the analyzer crystal, characterized in that the analyzer crystal (28) comprises two parts, being a first part (40) which has a reflective surface which is curved in one direction with a radius of curvature which is dependent on the location on the crystal, the second part (42) having a reflective surface which is curved with a constant radius of curvature (44) in the same direction.

2. An apparatus as claimed in claim 1, in which the first part (40) has a reflective surface which is curved in the form of a logarithmic spiral.

3. An apparatus as claimed in claim 1, in which a second part (42, 26) is provided at each of the two ends of the first part (40), said second part having a reflective surface which is curved with a constant radius of curvature (44, 48).

4. An analyzer crystal having a curved reflective surface (29) for wavelength analysis of X-rays, characterized in that the analyzer crystal comprises two parts, a first part (40) having a reflective surface which is curved in one direction with a radius of curvature which is dependent on the location on the crystal whereas the second part (42) has a reflective surface which is curved in the same direction with a constant radius of curvature (44).

5. An analyzer crystal as claimed in claim 4, in which the first part has a reflective surface which is curved as a logarithmic spiral.

6. An analyzer crystal as claimed in claim 4, in which a second part (42, 46) is provided at both ends of the first part (40), said second part having a reflective surface which is curved with a constant radius of curvature (44,48).

* * * * *